(12) United States Patent
Spell

(10) Patent No.: US 6,481,021 B2
(45) Date of Patent: Nov. 19, 2002

(54) COOLING HEADWEAR

(76) Inventor: Ronald C. Spell, 15206 Tacon La., Pflugerville, TX (US) 78660

( * ) Notice: Subject to any disclaimer, the term of this patent is extended or adjusted under 35 U.S.C. 154(b) by 0 days.

(21) Appl. No.: 09/923,271

(22) Filed: Aug. 6, 2001

(65) Prior Publication Data

US 2002/0035745 A1 Mar. 28, 2002

Related U.S. Application Data

(63) Continuation-in-part of application No. 09/668,577, filed on Sep. 25, 2000, now abandoned.

(51) Int. Cl.⁷ .................................................. A42B 1/06
(52) U.S. Cl. ............................... 2/209.13; 2/171; 2/172
(58) Field of Search .............................. 2/209.13, 203, 2/172, 172.1, 172.2, 195.1

(56) References Cited

U.S. PATENT DOCUMENTS

| 4,180,868 A | 1/1980 | Snow | 2/203 |
| 5,046,195 A | 9/1991 | Koritan | 2/172 |
| 5,327,585 A * | 7/1994 | Karlan | 2/7 |
| 5,557,807 A | 9/1996 | Hujar et al. | 2/171.2 |
| 5,669,075 A | 9/1997 | Weeks | 2/172 |
| 5,860,165 A | 1/1999 | Cvijanovich | 2/195.1 |
| 5,996,124 A * | 12/1999 | Asp, Jr. | 2/209.13 |
| 6,163,886 A * | 12/2000 | Carter | 2/172 |
| 6,185,750 B1 | 2/2001 | Dumas | 2/209.13 |

* cited by examiner

*Primary Examiner*—John J. Calvert
*Assistant Examiner*—Alissa L. Hoey
(74) *Attorney, Agent, or Firm*—Christopher J. Whewell

(57) ABSTRACT

Provided herein are articles of headwear that comprise a pouch portion which may be charged with ice. Ice so charged is caused to melt under the effects of ambient temperature and is caused to drip from the pouch portion onto the neck of a person wearing such article. According to a preferred form of the invention, the head of a wearer is not contacted by ice or water during use of such article.

28 Claims, 7 Drawing Sheets

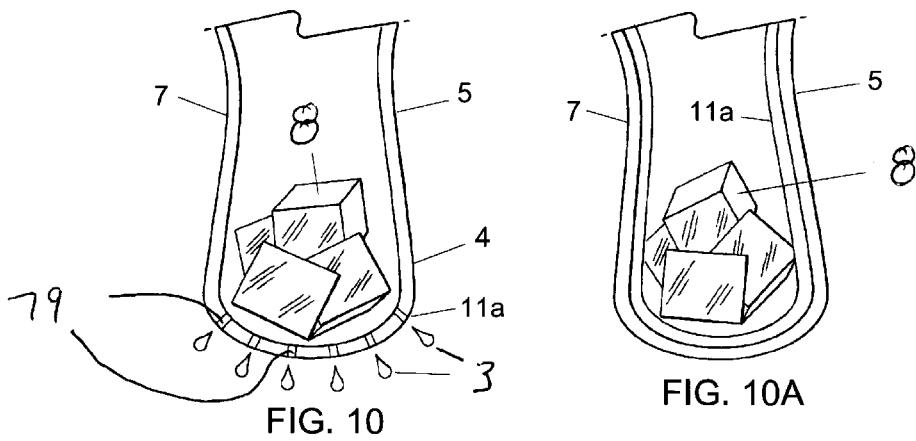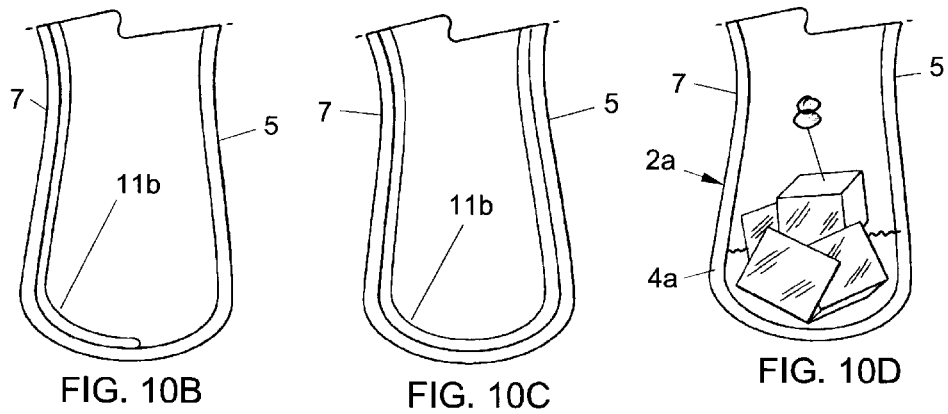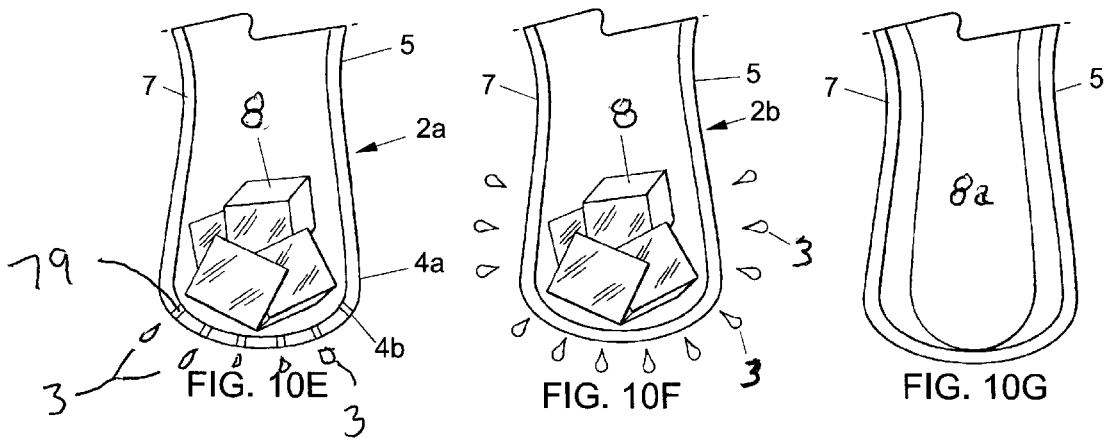

COOLING HEADWEAR

CROSS-REFERENCES TO RELATED APPLICATIONS

This application is a Continuation-In-Part of U.S. patent application Ser. No. 09/668,577 filed on Sep. 25, 2000, now abandoned now the entire contents of which are herein incorporated fully by reference thereto.

TECHNICAL FIELD

This invention relates to headwear that provides its wearers with relief from the effects of sun, wind, and perhaps most importantly, heat. More particularly, it relates to headwear into which a cooling substance such as ice may be contained and in which the course taken by the liquid water that results from the melting of the ice is controlled to a desired location on the body, preferably the neck of the wearer.

BACKGROUND

Various articles of headgear purportedly useful for protecting its wearers from many environmental factors such as heat, cool, solar rays, wind, blowing sand, etc. have been devised and disclosed in the prior art. The following U.S. Patents are useful to illustrate but a few of the prior art teachings concerned with such articles:

U.S. Pat. No. 1,567,931 discloses a compress having a plurality of layers of absorbent material on one side and a rubber lining on the other side and having a longitudinal seam along the bottom and two seams extending upwardly from the ends thereof, to unite the several layers of materials along the seams and form a pocket, in which the pocket is open at the top so as to be capable of receiving ice or water.

U.S. Pat. No. 3,029,438 provides a headband comprising a visor having an annular sweat-band attached to the visor. The sweatband includes an annular strip made of thin malleable metal foil having an inwardly presented face and an outwardly presented face. The inwardly presented face is adapted for contact directly against the brow and head of the wearer. There is a water saturable sponge layer positioned facewise against the outwardly presented face of the strip which is slightly narrower than the strip so that its longitudinal margins extend in inwardly spaced parallel relation to the longitudinal margins of the strip. There is a fabric layer disposed against the outwardly presented case of the sponge layer and extending inwardly around the longitudinal margins thereof for flatwise overlying contact against the projecting portions of the strip. There are also a pair of hems extending enclosingly around and being stitched to the fabric layer and strip in the region where the fabric layer and strip are in overlying engagement.

U.S. Pat. No. 3,889,684 teaches a pack for therapeutic heat transfer with portions of the human body which comprises a substantially fluid impervious envelope, heat transfer means enclosed therein, and a porous flexible cover therefor surrounding the envelope, in which the cover comprises: a) a flat sheet member folded along a fold line to provide a pair of superimposed members, the members being detachably fastened along the edges thereof beyond the fold line to permit ready insertion and removal of the pouch; b) a plurality of flexible strap means attached to the cover member having detachable fastening means at the end of each; and c) cooperating fastening members attached to the body of the cover at points remote from the strap members to permit attachment of the heat exchange assembly to a body member.

U.S. Pat. No. 4,180,868 teaches a hat accessory which has a rear piece 11 which in FIG. 2 therein is shown to include an outer material layer 14 which is sized in length 16 to extend from above the rim 18 of the hat. The outer layer 14 is sized in width 20 to extend around the rim 18 of the hat 12 rearward between about the temples of the user, as shown in FIG. 1. the outer layer 14 may be water-repellant or fire-retardant material. The accessory also has an inner layer 22, which is secured to the outer layer 14 along the edges thereof, to form a pocket 28 (FIG. 4) that is sized in length from about the upper edge 24 of the outer layer 14 to about the collar area 30 (FIG. 1) of a user when the accessory is adapted to the hat 12. The inner layer 22 is made of a mesh-like cloth, to avoid chaffing and to absorb perspiration during hot weather or exertion. In this accessory, there is disclosed an insert 32 that is adapted to be fit inside the pocket 28, which insert is preferably formed of a pliable liquid-absorbent material so that in periods of warm weather it may be soaked in a liquid such as water to provide evaporative cooling to the wearer.

U.S. Pat. No. 4,641,655 provides a cooling wrap that includes: a) an elongated strip of water-pervious fabric forming a central pouch section with tying straps at both ends, the pouch section being formed by a single fold of the sides of the strip of fabric and the tying straps being formed by stitching the single folds together; b) an elongated bag formed of water pervious fabric secured in the pouch section, the bag having an open-pored foam liner along at least one side; and c) a closure means for the bag, whereby the cooling wrap may be tied around a portion of the body and a frozen water medium placed in the bag will have body heat transferred thereto resulting in a controlled dispensing of water through the foam liner and fabric to the body portion.

U.S. Pat. No. 5,054,122 discloses a hat having a head covering including: a) a portion adapted to be disposed adjacent the forehead of a wearer, this portion having an inwardly opening channel on the inner surface thereof, b) a plurality of cooling elements disposed within the channel, the cooling elements each having opposite ends, the ends of adjacent cooling elements being spaced from one another to define gaps therebetween; c) a ventilating socket disposed inwardly of the cooling elements, the ventilating socket having a plurality of vent holes formed therethrough, and wherein the ventilating socket has a plurality of spaced outwardly extending strips thereon, the strips being fastened within the gaps.

U.S. Pat. No. 5,197,292 sets forth a headwear device for cooling the wearer, that includes: a) a cap having an interior surface and exterior surface, the cap having at least one opening to at least one defined compartment chamber within, the chamber formed therewithin by the interior surface of the cap and an exterior surface of the cap; and b) the chamber interior adapted to contain ice and having at least one surface comprising means for transmitting fluid melted ice from the chamber interior through the caps interior surface and dripping the fluid at a moderate rate onto the head of the wearer.

U.S. Pat. No. 5,557,807 teaches an article of headwear having coolant means removably supported therein, which includes in its construction: a) headwear having at least a crown section designed to cover the top of a head of a wearer, the crown section including at least a dome, front, and left and right sides; b) at least one pouch secured inside the crown; c) the coolant means comprising a pliable closure means containing a liquid adapted to be refreezable, the coolant means shaped to be received and stored in the pouch, wherein the pouch is constructed of a first layer of a first material and a second layer of second material, the second material different from the first material, the first layer of material provided on the outside of the pouch and being a thin material having good thermal transmissive properties, and the second material provided interior of the first material and having thermal insulative properties.

U.S. Pat. No. 5,822,800 discloses a multi-functional hat comprising: a) a substantially tubular hat body with an upper edge and a bottom edge; b) a tubular drawstring channel formed along the upper edge and encircling the tubular hat body for enclosing a drawstring; c) a drawstring positioned in the drawstring channel, the drawstring having opposed ends passing outwardly to exterior the hat body; d) a domal head covering attached to the tubular hat body near the upper edge; and e) an opening in a front portion of the head covering, the opening comprising a face opening.

U.S. Pat. No. 5,940,880 teaches an apparatus for providing coolant water to the head of a user during exercise or other strenuous activity, which includes in its construction: a) a water bladder, the water bladder having flexible walls that collapse when empty to form a generally flat profile; b) an air bladder, the air bladder having flexible walls that collapse when empty to form a generally flat profile, the air bladder positioned in parallel planar orientation with the water bladder, c) a flexible envelope, the flexible envelope configured to receive the water bladder and the air bladder in the parallel planar orientation through an opening on a first end of the envelope, the envelope further configured to restrict expansion of the air bladder and the water bladder when each of the bladders are filled; d) an irrigation conduit, the conduit positioned about the head of the user in a manner that permits flow of water therefrom onto the head of the user; e) a water conduit connecting the water bladder to the irrigation conduit; and f) means for pressurizing the air bladder, wherein pressurization of the air bladder forces water from the water bladder through the water conduit into the irrigation conduit in a manner that dispenses water from the irrigation conduit onto the head of the user.

Of these and other devices, hat accessories, etc. of the prior art, however, none has thus far provided any headwear which contains a flap portion that the user may charge with ice, wherein the ice is caused to melt under the effect of ambient heat and in which the liquid water resulting from the melting of the ice may under the effect of gravity be caused to fall to the wearer's body in a desired location. Even U.S. Pat. No. 4,180,868, while providing an accessory with a pouch into which a water-soaked insert may be placed, is not configured so that a portion of the a panel of its construct beneath which lies the pocket is disposed to be in direct contact with the neck of the wearer. No headwear or hat accessory of the prior art provides a pouch portion which is adapted to Is contain ice, in which the bottom of the pouch touches the neck of the wearer so that as the ice melts, the water so formed is caused to penetrate the panel(s) and immediately contact the neck of the wearer upon its exit from the panel(s). Further, none of the prior art provides such an article which simultaneously protects the wearer from the effects of the sun's rays. Finally, none of the prior art provides such a device which accomplishes the foregoing while shielding the wearer from the effects of the wind. The present invention provides headwear articles having these features.

SUMMARY OF THE INVENTION

According to the present invention there is provided a headwear article useful for cooling its wearer which comprises a head fitment portion and a pouch portion. The pouch portion includes a first panel disposed towards the neck of the wearer and a second panel disposed away from the neck of the wearer. The panels are attached to one another so as to provide the pouch with an interior portion between said panels which is adapted to contain ice. The pouch has an upper portion and a lower portion, and the pouch is affixed to the head fitment portion at the upper portion, such that a portion of the first panel beneath which lies said interior portion is disposed to be in direct contact with the neck of the wearer. The pouch portion is affixed to the head fitment portion of an article of headwear at the upper portion of the pouch. Under such an arrangement, the ice in the pouch is caused to be melted under the effects of ambient heat and the melted ice drips out of the pouch portion at its lower edge, and onto the neck and back of the wearer. The cooling effect of the water being continuously applied to the neck and back of the wearer provides comfort on hot days, or during work or exercise activities. The head fitment portion of the invention may include any article of headwear known in the art.

BRIEF DESCRIPTION OF THE DRAWINGS

FIG. 10 is a partial sectional view showing melting ice exiting the lower portion of the pouch through perforations;

FIG. 10A is a partial sectional view showing melting ice contained within the pouch;

FIG. 10B is a partial sectional view showing insulating material against the first panel portion, for the purpose of preventing ice burn to the neck of the wearer against which the first panel contacts;

FIG. 10C is a partial sectional view showing an insulating material lining the pouch;

FIG. 10D is a partial sectional view showing melting ice contained in a plastic pouch;

FIG. 10E is a partial sectional view showing melting ice exiting the lower portion of the plastic pouch;

FIG. 10F is a partial sectional view showing the passage of water through the walls of the pouch;

FIG. 10G is a partial sectional view showing the pouch containing an ice pack;

DETAILED DESCRIPTION

Figure 1:
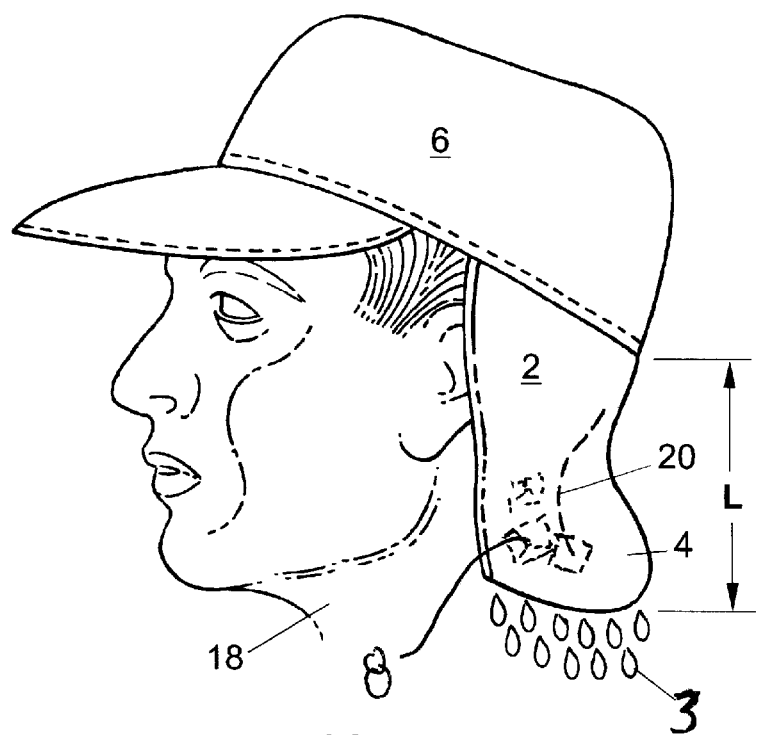
FIG. 1 is a side perspective view of an article according to one form of the invention in position about its wearer.

Referring to the drawings and initially to FIG. 1 there is shown a side perspective view of an article according to one form of the invention in its normal position about a wearer of the article. In this figure is shown a head fitment portion 6, pouch portion 2, ice 8, and wearer 18. In such an embodiment, ice that has been previously charged to the interior of pouch portion 2 is caused under the influence of ambient heat to melt to form droplets of cold water 3 which under the force of gravity come into contact with the nape 20 of the neck of the wearer 18 to effect cooling of the wearer.

The head fitment portion 6, in its simplest form, may merely be a band of material which is rigidly and removably affixed and coextensively extended about a person's head, which covers at least a portion of the temple region. Such an arrangement is well-exemplified by the well-known sweat band, which athletes often wear to keep sweat from interfering with their vision. Such an arrangement is also exemplified by a piece of headwear commonly referred to as a visor by those skilled in the art, such visors having an elastic band that is adapted to hug the wearers head. Often, visors are not completely closed, i.e., they do not completely circumscribe the wearer's head, such as the embodiment in FIG. 4; however, such lack of closure does not adversely affect the visor's ability to function in connection with the present invention. Other forms of headwear which are not completely closed are as suitable for use in the invention as those which are completely closed.

Such a coextensive arrangement is also exemplified by a piece of headwear commonly referred to as a "baseball cap" by those skilled in the art, such caps having an portion that is adapted to hug the wearers head. Such an arrangement is also exemplified by a piece of headwear commonly referred to as a cowboy hat by those skilled in the art, such cowboy hats having an portion that is adapted to hug the wearers head. In fact, all pieces of headwear that the present invention is useful in conjunction with each contain a head fitment portion, which includes a head fitment portion that extends coextensively about the wearers head and passes over the temple region and generally above the ears. Thus, the words "head fitment portion" as used in this description and the appended claims means that portion on any and all types of headwear which circumscribes the upper portion of the head of the wearer and passes about the temple region, whether the headwear be baseball caps, visors, sweatbands, bucket hats, construction helmets, cowboy hats, etc., and in each case the head fitment portion includes an inside surface portion which contacts the wearer's head and an outside surface portion which faces away from the wearer's head, although often the outside surface portion is stitched or otherwise affixed to the interior of the hat.

Figure 2:
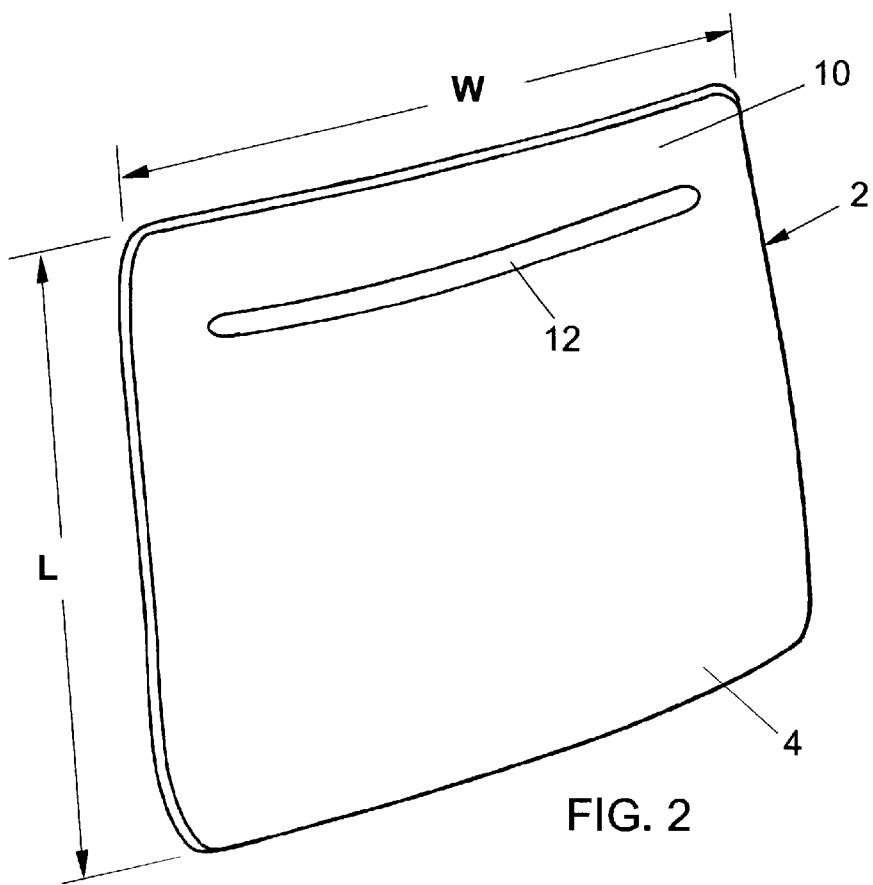
FIG. 2 is a perspective view of the pouch portion of an article according to the invention.

The pouch portion 2 is described in greater detail in FIG. 2 in which are shown its upper portion 10, lower portion 4, and charging hole 12. In general, the pouch portion is merely a pouch made by affixing two panels to one another along their outer perimeters, and which is thus adapted to contain ice by virtue of the creation and existence of the interior volume defined by the space between such panels. Thus, the pouch comprises a first panel disposed towards the neck of the wearer and a second panel disposed away from the neck of the wearer. The panels are attached to one another so as to provide said pouch with an interior portion between said panels which is adapted to contain ice. The pouch has an upper portion and a lower portion, and the pouch is affixed to the head fitment portion at the upper portion so that at least a portion of the first panel beneath which the interior portion lies is disposed to be in direct contact with the neck of the wearer.

Such pouch portions useful in accordance with the invention have an opening portion 12 into which ice may be charged. An opening portion 12 may be located on either or both of the panels of its construction, and is in one preferred form of the invention provided with a means for closing the pouch once the ice has been charged. Such means for closing may include a zipper, hook-and-loop type fasteners, a button, etc., or any other means for effecting a closure of such an opening as are recognized by those skilled in the textile arts. The exact location of the opening portion is not critical to the functionality of the present invention, and the opening portion may be located anywhere on the pouch. FIGS. 9, 9A–C show embodiments having the opening portion through which ice is caused to be disposed within the pouch at an alternate location.

Since the invention involves affixing the pouch portion to a head fitment portion at the upper portion 10 of the pouch portion 2, and since the affixing operation may employ stitching, it is a natural consequence that some, albeit in many instances a minute, of the surface area of the pouch will be lost to the stitching. Thus, in many instances at least a tiny amount of the inner volume of the pouch portion will be unavailable to contain ice because of this stitching, and because of stitching used to join the panel portions to one another when stitching is used for such (although the present invention contemplates a pouch portion of singular construction, such as a perforated plastic bag affixed to a head fitment portion in analogous fashion as to a pouch as disclosed herein.) It is usually desirable to maximize the ice-bearing capacity of a pouch in accordance with the invention, since the time for which an article according to the invention shall remain effective as providing extra cooling is a function of its ice carrying capability, and because it is not always desired to fully load the pouch, i.e., it is better to have the space and not need it than vice versa. Thus, in one preferred embodiment the volume between the panels from which the pouch is constructed is entirely capable of containing ice. In such an ideal instance, it could be said the interior portion that is adapted to contain ice is of such size that 100% of the surface area of the panels is used in defining the dimensions of the interior portion. In other instances, such as where the length dimension L of FIG. 1 is, say, 10 inches, and the amount of upper portion of the pouch portion which is affixed to the head fitment portion is one inch, then the entire volume of the interior portion of the panels lie beneath 90% of the surface area of the panels.

For purposes of this invention, any percentage of the surface area of the panels may be used in defining the dimensions of the interior portion, but it is preferable that the entire volume of the interior portion of the panels lie beneath more than 30% of the surface area of the panels. It is more preferable that the entire volume of the interior portion of the panels lie beneath more than 50% of the surface area of the panels. It is more preferable still that the entire volume of the interior portion of the panels lie beneath more than 70% of the surface area of the panels. It is even more preferable that the entire volume of the interior portion of the panels lie beneath more than 90% of the surface area of the panels. It is most preferable that the bottom edge portion 4 of the pouch be coincident with the lowermost portion of the interior portion, i.e., that the panels used in constructing the pouch are of the same length dimension.

In yet another embodiment of the invention where it is preferable that more than 95% of the surface area of the panels is used in defining the dimensions of the interior portion, the pouch portion may be affixed to the head fitment portion using a fastening means that does not inhibit the amount of interior volume of the pouch which is capable of receiving ice, as defined by the outer surface area. Such a fastening means include without limitation a hook-and-eye type fastener, button, zipper, or any fastening means known in the art.

The selection of a particular dimension for the pouch portion is a matter of practical and aesthetic choice, with the possibilities being only limited by the designer, and which possible geometries include: rectangular, trapezoidal, rhombohedral, circular, semicircular, etc. However, according to one preferred form of the invention, the pouch portion is rectangular in dimension.

The length dimension of the pouch portion L, as shown in FIGS. 1 and 2 may be of any selected length, however, it is most desired that the length of the pouch be just sufficient to contact the wearer's neck and in this regard the preferred length dimension will vary, depending upon individual measurements. However, a length dimension of any value between 3.00 inches and 16.00 inches, including every hundredth inch therebetween, are useful in accordance with the invention.

Figure 3:
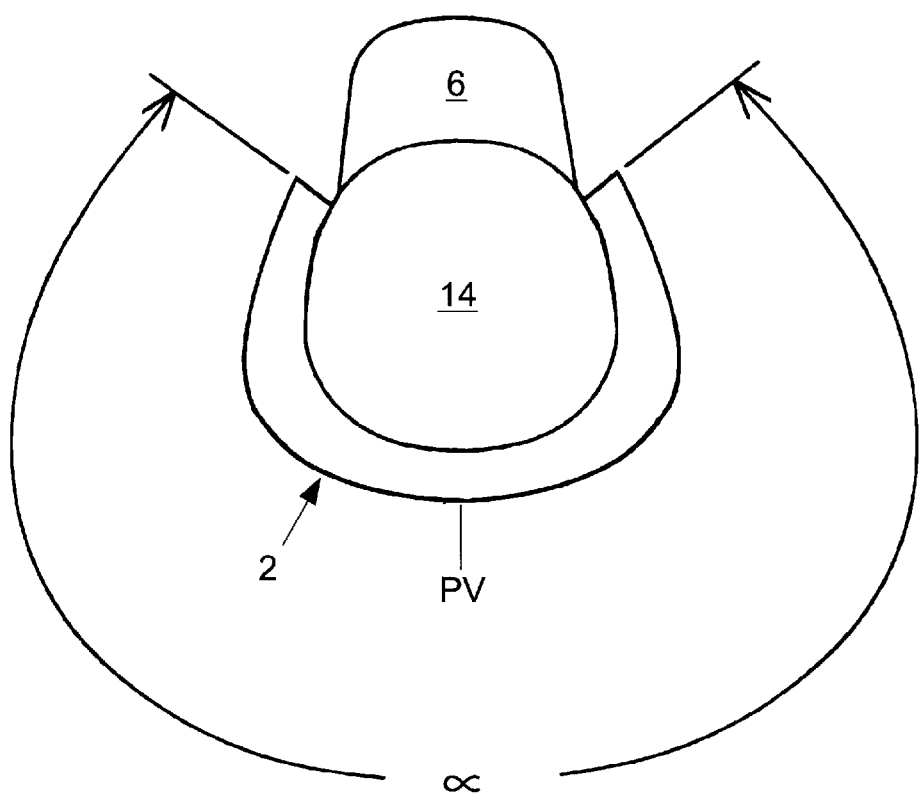
FIG. 3 is an overhead view of an article according to the invention disposed about the head of a wearer.

The width dimension of the pouch portion L, as shown in FIG. 2 may be of any selected width, but is conveniently defined in terms of the angle $\alpha$ in FIG. 3. In FIG. 3, the wearer's head 14 is shown with a baseball cap serving as the head fitment portion 6. In this figure, the pouch portion 2 extends about the head fitment portion for an amount $\alpha$, as measured in degrees. For purposes of the present invention the angle a may be any value between 30 degrees and 300 degrees, including every degree therebetween, with the location of the vertex of the angle $\alpha$ not being of absolute consequence: However, it is in most cases preferred that the vertex of the angle a be located at the direct rear of the wearer's head, as such preferred vertex location is denoted by the letters PV in FIG. 3. In one preferred form of the invention, the angle alpha $\alpha$ is about 180 degrees. Thus, the actual width dimension may vary with the measurements of the head of each individual wearer, but the width dimension of the pouch portion of the present invention is conveniently expressed in terms of the angle $\alpha$ for all wearers.

In one preferred form of the invention, the bottom of the interior portion coincides with the lower portion of the pouch. Such an arrangement is beneficial for precluding any of the melted ice from contacting the wearer's head, since the melted ice may then only fall under the influence of gravity directly onto the neck of the wearer. The result of having none of the melted ice coming into contact with the wearer's head and even neck may be insured by constructing the panel of the pouch which is nearest to the wearer from a material which serves as a moisture barrier between ice in the pouch portion and the wearer's head. Stated another way, the panel from which the pouch is constructed that is facing the wearer's head may be a moisture-impervious sheet, or it may be a fabric which is laminated or treated on the side which resides in the interior of the pouch. In such embodiment, none of the melted ice could contact the head or the neck of the wearer. Such moisture barriers are well known in the art and include sheets comprised of various polymeric materials, metal foils, treated fabrics, etc. Thus, the present invention contemplates the use of a pouch material which does not permit the passage of water through its walls and which may be charged with ice in accordance with the invention. The result of such an embodiment is that such a pouch provides cooling by virtue of its contact and proximity to the neck of the wearer, but does not provide a liquid coolant that drips out of the pouch 2 and contacts the wearer's skin. In yet another embodiment, the invention comprises a pouch portion attached to a head fitment portion as previously described, but the ice to be charged to the pouch portion, rather than being directly placed into the pouch portion, is first placed into a sealable plastic bag or other functionally-equivalent container, such as a ZIPLOC® storage bag. Then, the plastic bag or the like is placed into the pouch portion. In this embodiment, water from the melted ice does not escape the pouch portion.

In another form of the invention the panel of the pouch which is nearest to the wearer comprises a material which is insulative in nature, so as to serves as a thermal barrier between ice in the pouch portion and the wearer's head. Such embodiment is useful for alleviating numbness caused by the proximity of ice to the wearer's head under certain climactic conditions. Alternatively, one or more of the panels from which the pouch is constructed may comprise an insulative barrier to control the rate of melting of the ice. Sufficient such thermal barriers are well known to those skilled in the art of insulative materials.

The material of construction of the head fitment portion 6 and the pouch portion 2 according to the invention may each independently be any material known to those in the textile arts as being a useful material from which an article of headwear may be made, including without limitation felt, natural fibrous materials, synthetic fibrous materials, thermoplastic polymers, thermoset polymers, including without limitation cotton, polyester, SUPPLEX®, etc. According to one preferred form of the invention the material chosen permits the passage of liquid water through its bottom portion 4 so that such water can then effect cooling of the wearer 18 by dripping onto the wearer's neck 20. However, it is most preferred that the material from which these elements are constructed is readily washable in a washing machine and is preferably comprised of a natural fabric, such as cotton or linen for both a head fitment portion 6 and a pouch portion 2 according to the invention.

The means of attachment of the upper portion 10 of the pouch portion 2 to the head fitment portion 6 may be any means of attachment recognized by those of ordinary skill in the textile industry as being suitable for affixing materials used in providing a final headwear article. Such means include without limitation, stitching, riveting, fusion, hook-and-loop type fasteners, snaps, buttons, hot melt glues, zippers hook-and-eye type fasteners, etc. It is most preferred, however, that the top portion 10 of a pouch element 2 according to the invention be attached to the head fitment portion 6 by stitching the pouch portion to the head fitment portion, either on the inside portion of the head fitment portion or the outside portion of the head fitment portion.

Figure 4:
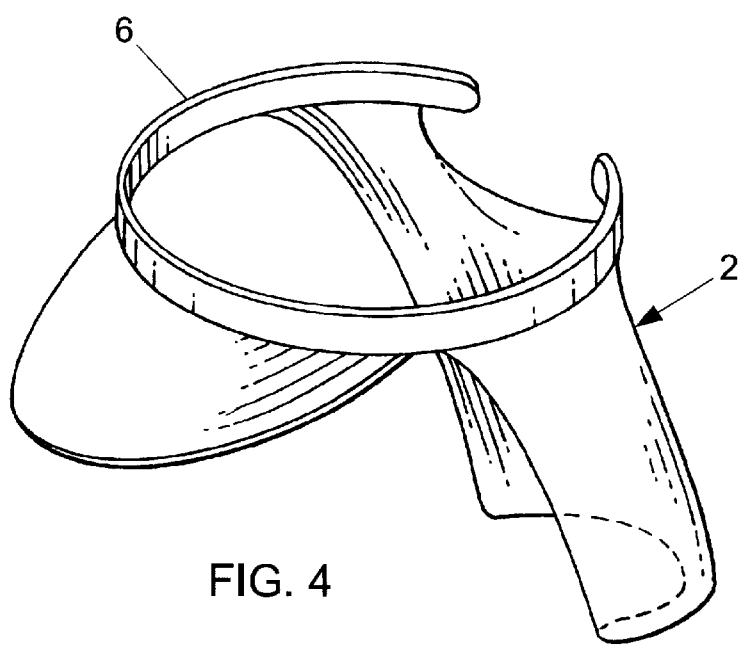
FIG. 4 is a perspective view of a visor according to the invention.

FIG. 4 shows an alternative form of the invention comprising a visor, to which a pouch is affixed in accordance with the invention.

Figure 5A:
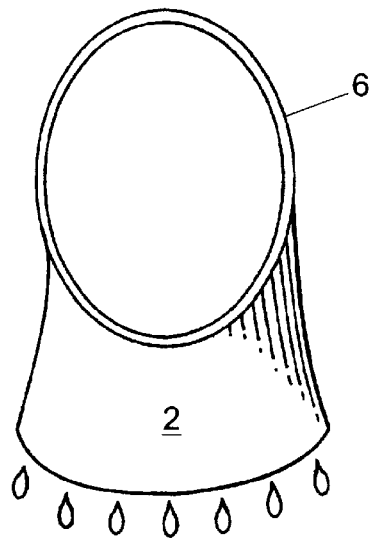
FIG. 5A is an overhead view of an alternate embodiment of an article according to the invention in which the head fitment portion is a sweatband or headband.

FIG. 5A shows an alternative embodiment of the invention in which the head fitment portion 6 is comprised of elastic of the type commonly employed in making headbands, as such material is well-known to those skilled in the art. In this embodiment, the head fitment portion circumscribes the crown of the head of the wearer, passing over the temples and generally over the ears, and the pouch portion 2 is affixed to such sweatband by any means described elsewhere herein for attaching the head fitment portion to the pouch portion.

Figure 5B:
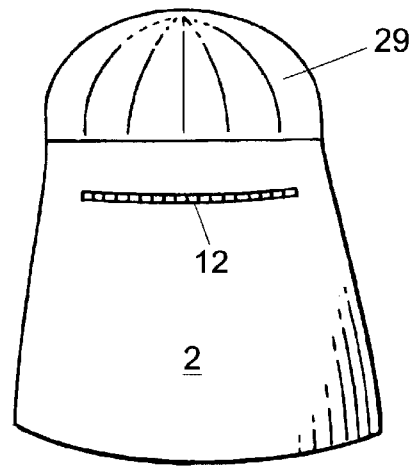
FIG. 5B is a rear view of an alternate embodiment of an article according to the invention in which the head fitment portion comprises a baseball cap.

FIG. 5B shows an alternative embodiment of the invention in which the opening 12 through which ice may be charged into the pouch portion 2 is disposed on the surface of the pouch that faces away from the wearer, and is disposed horizontally. In this embodiment is also shown the top of the hat portion 29.

Figure 5C:
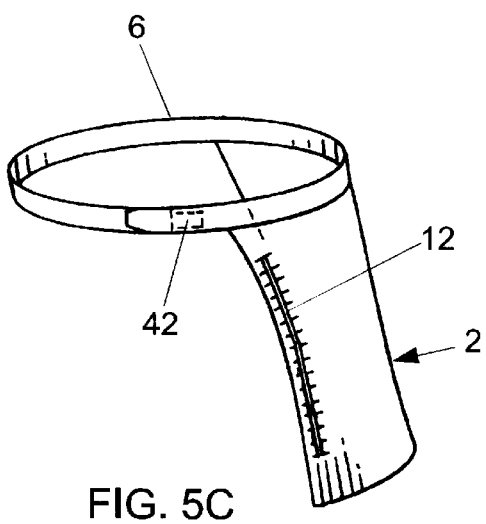
FIG. 5C is a side view of an alternate embodiment of an article according to the invention in which the head fitment portion comprises a sweatband or headbane.

FIG. 5C shows an alternative embodiment of the invention in which the opening 12 through which ice may be charged into the pouch portion 2 is disposed on the surface of the pouch that faces away from the wearer, and is disposed vertically. In this embodiment, the head fitment portion 6 comprises a single strap of material which is joined to itself at its ends by a fastening means 42 which is preferably a hook-and-loop (i.e., VELCRO®) type fastener, although other fastening means known in the art are functionally equivalent. The exact location of the fastening means with respect to the head of the wearer is not a critical aspect of the invention, but it is most preferable that such fastening means 42 is disposed to the rear of the head fitment means. Such embodiment permits the wearer to also wear any ordinary hat of their choice by first affixing such article according to this invention to their head, and then merely placing said ordinary hat on their head over such cooling headwear.

Figure 6:
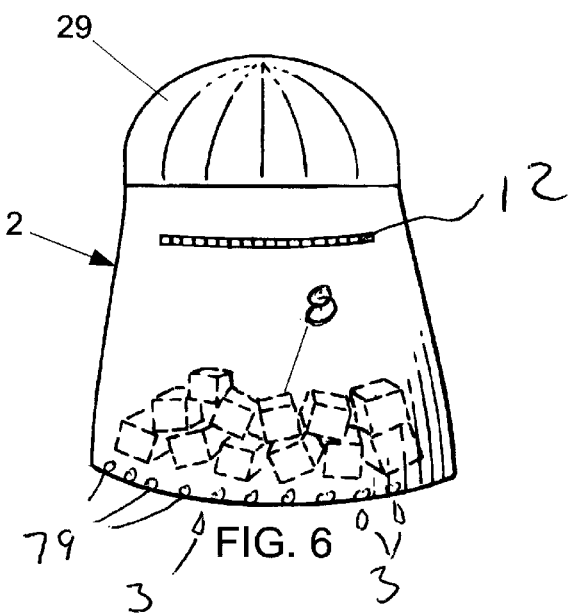
FIG. 6 is a rear view of an alternate embodiment of an article according to the invention in which the head fitment portion comprises a baseball cap, showing the location of ice within the pouch portion.
Figure 7A:
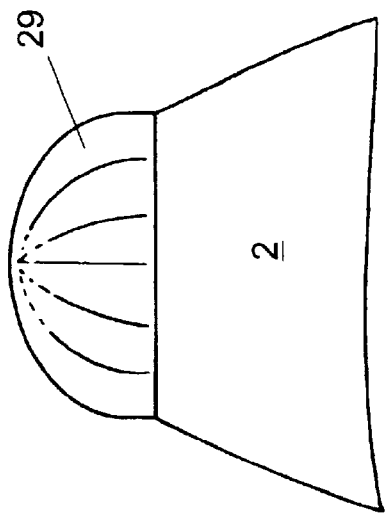
FIG. 7a shows an alternate embodiment of the invention in which the pouch portion is triangular.
Figure 7C:
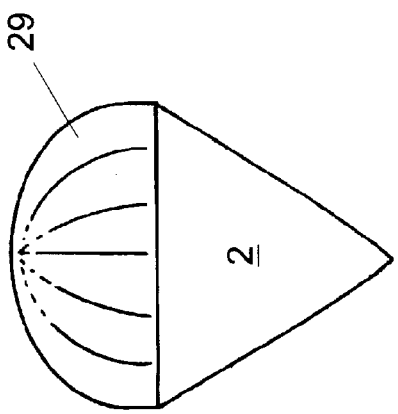
FIG. 7c shows an alternate embodiment of the invention in which the pouch portion is a shaped like a parallelogram.
Figure 7B:
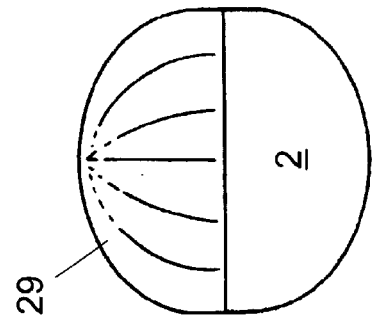
FIG. 7b shows an alternate embodiment of the invention in which the pouch portion is trapezoidal.
Figure 7D:
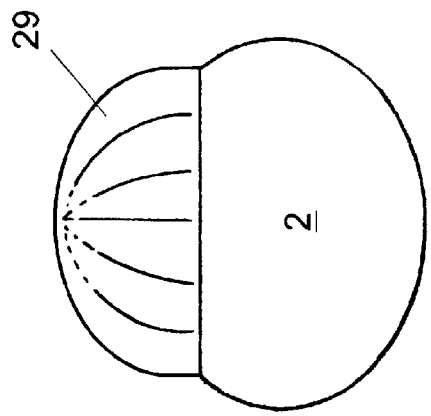
FIG. 7d shows an alternate embodiment of the invention in which the pouch portion is oval.
Figure 7E:
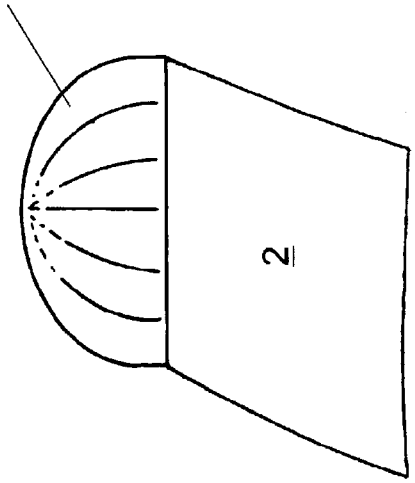
FIG. 7e shows an alternate embodiment of the invention in which the pouch portion is semi-circular.

FIG. 6 shows an alternate form of the invention when the pouch portion 2 comprises a plastic bag having an upper portion and a lower edge portion, and having perforations 79 disposed along its lower edge. FIGS. 7a, 7b, 7c, 7d, and 7e each depict alternate forms of the invention in which the shape of the pouch portion is triangular, trapezoidal, rhombohedral, circular, and semicircular, respectively.

Figure 8:
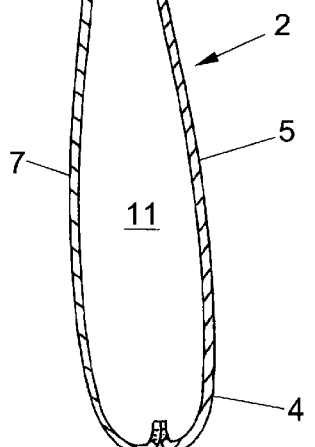
FIG. 8 is a sectional view showing the pouch portion comprised of two panels and having an interior portion.
Figure 9:
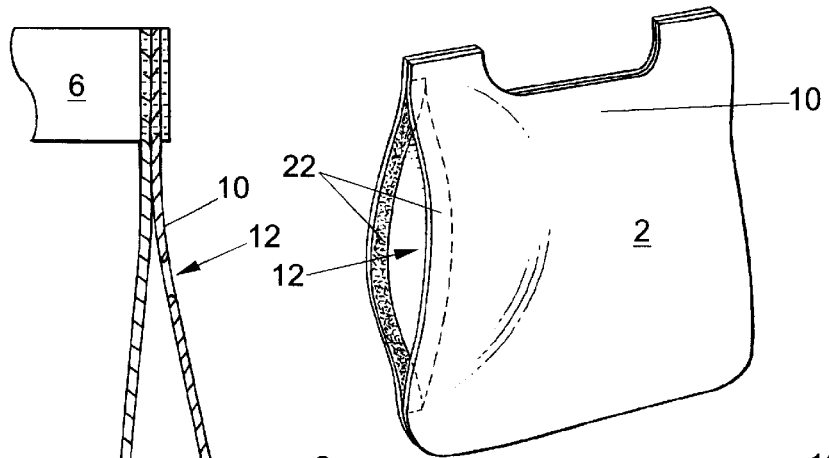
FIG. 9 is a perspective view of an alternative form of the invention showing the charging hole closing comprising a hook and loop (i.e., "VELCRO®") means.
Figure 9A:
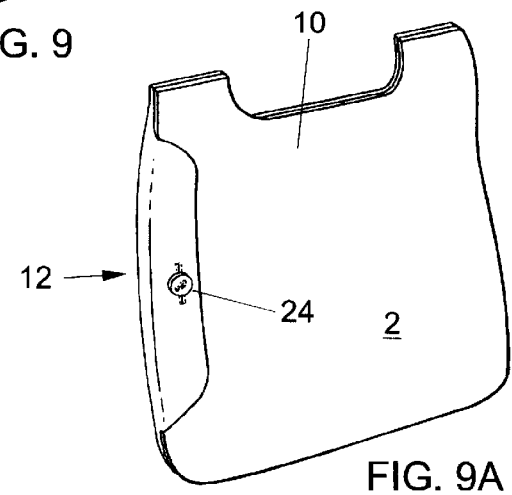
FIG. 9A is a perspective view of an alternate form of the invention showing the charging hole closure means to be a button means.
Figure 9B:
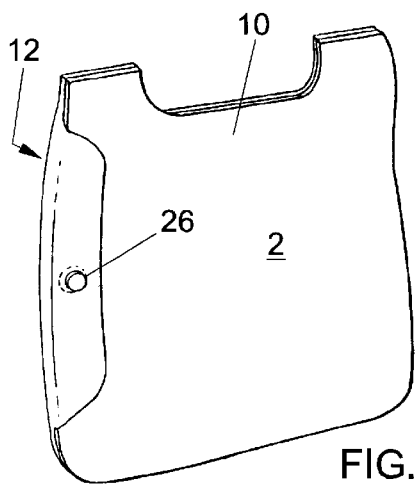
FIG. 9B is a perspective view of an alternate form of the invention showing the charging hole closed with a hook and eye means.
Figure 9C:
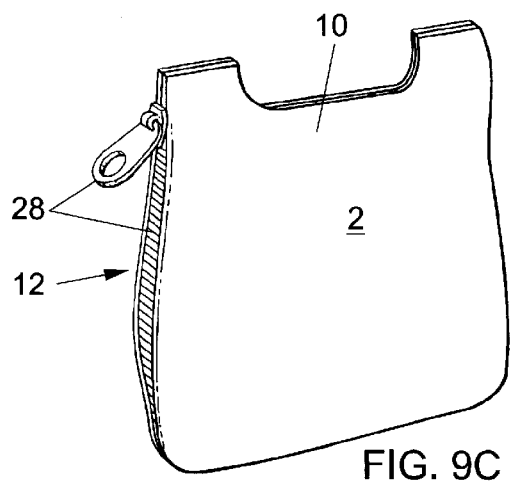
FIG. 9C is a partial sectional view showing the charging hole closed with a zipper means.
Figure 11:
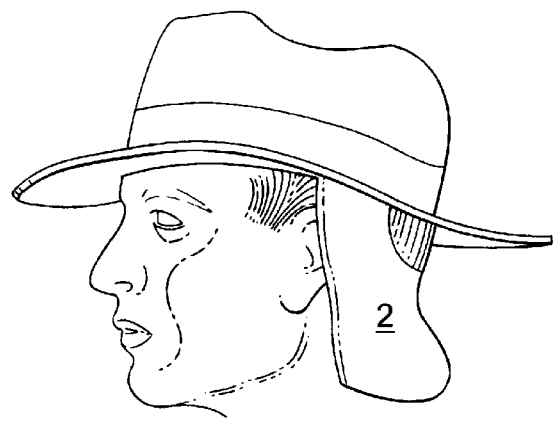
FIG. 11 is a side view showing the invention attached to a cowboy hat.
Figure 11A:
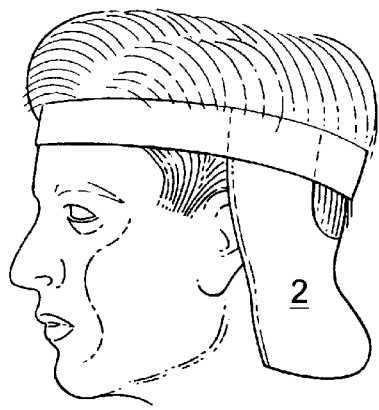
FIG. 11A is a side view showing the invention attached to a sweat band.
Figure 11B:
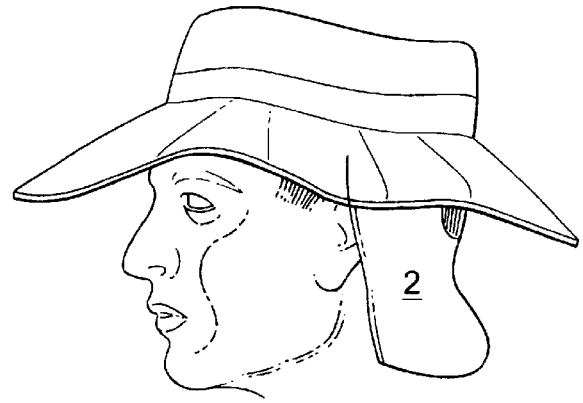
FIG. 11B is a side view showing the invention attached to a bucket hat.
Figure 11C:
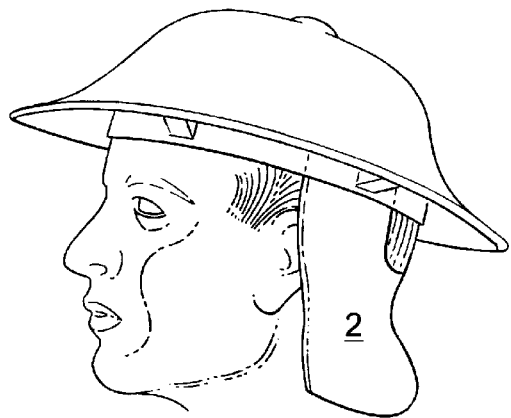
FIG. 11C is a side view showing the invention attached to a hard hat.
Figure 11D:
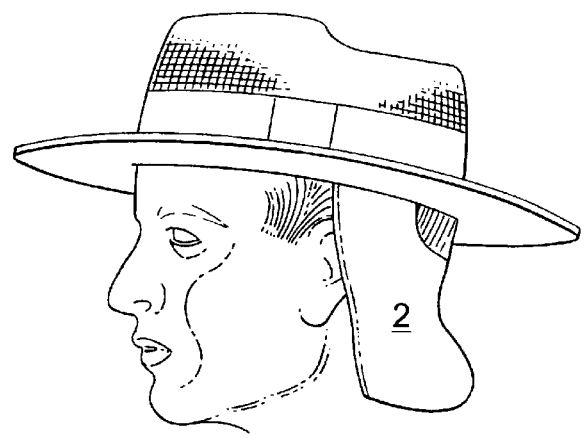
FIG. 11D is a side view showing the invention attached to a straw hat.

FIG. 8 is a sectional view showing the pouch portion comprised of two panels and having an interior portion. The first panel portion 7 is disposed to face the neck of the wearer, and the second panel portion 5 is disposed to not contact the wearer. The interior portion 11 is adapted to contain ice, which may be charged into the interior portion through hole 12. Head fitment portion 6 is also shown.

FIGS. 9, 9A, 9B, and 9C are perspective views of alternative forms of the invention showing the charging hole closing comprising a hook and loop (i.e., "VELCRO®") means, a button means, hook and eye means, and zipper mean, respectively, although any closure means known in the art may be employed. Although the opening portion comprising the closure means in each of these figures is shown to be at a side location where the first and second panels meet, the opening portion may be located along any edge of where the two panels meet, and may also be an opening that is exclusively located on only one of either of said first or second panels. In a preferred embodiment, the opening is disposed along a side as shown in the figures. Choice of the exact closure means is within the desire of the user as such, while being functional, the choice of which is a matter of personal taste in convenience.

FIG. 10 is a partial sectional view showing melting ice 8 exiting the lower portion of a pouch according to the invention through perforations 79 as water 3. FIG. 10A is a partial sectional view of a pouch according to the invention showing melting ice contained within the pouch, wherein the ice is contained within a water-resistant material 11a, such as a ZIPLOC® bag, and is thus unable to drip through the panels themselves. FIG. 10B is a partial sectional view of a pouch according to the invention showing insulating material 11b against the first panel portion that is to be disposed towards the neck of the wearer of an article according to the invention, to prevent ice burn to the neck of the wearer against which the first panel contacts. FIG. 10C is a partial sectional view showing an insulating material 11b lining the interior of a pouch portion according to the invention. FIG. 10D is a partial sectional view showing melting ice contained in a plastic pouch, which is an embodiment according to the invention in which the first and second panel portions are both made of a plastic material. FIG. 10E is a partial sectional view of an embodiment in which the pouch portion 2a is a plastic bag with perforations 79 at its bottom and showing melting ice exiting its lower portion. FIG. 10F is a partial sectional view showing the passage of water through the walls of the pouch in cases where the first and second panels are a woven fabric that permits water passage, such as cotton, polyester, etc. FIG. 10G is a partial sectional view showing a pouch according to the invention containing an ice pack 8a disposed in its interior portion.

FIGS. 11, 11A, 11B, 11C, and 11D are side views showing the invention in various embodiments in which the head fitment portion includes a cowboy hat, sweat band, bucket hat, hard hat, and straw hat, respectively.

Although the cooling means used as a material which is to be charged into a pouch portion according to the invention has thus far been described as ice, the present invention contemplates the use of ice packs or coolant filled pouches in the stead of ice as used herein. In such embodiment, however, the cold fluid in such ice pack or coolant filled pouch is confined and is thus unable to provide a liquid coolant which drips out of the pouch portion 2 and contacts the wearer's skin. FIG. 10G is illustrative of such embodiment.

Consideration must be given to the fact that although this invention has been described and disclosed in relation to certain preferred embodiments, obvious equivalent modifications and alterations thereof will become apparent to one of ordinary skill in this art upon reading and understanding this specification and the claims appended hereto. Accordingly, the presently disclosed invention is intended to cover all such modifications and alterations, and is limited only by the scope of the claims which follow.

I claim:

1. A headwear article useful for cooling its wearer comprising:
   a) a head fitment portion; and
   b) a pouch portion having an opening portion through which ice may be charged into said pouch,
   wherein said pouch comprises a first panel disposed towards the neck of the wearer and a second panel disposed away from the neck of the wearer, said panels being attached to one another so as to provide said pouch with an interior portion between said panels which is adapted to contain ice, said pouch having an upper portion and a lower portion, and wherein said pouch is affixed directly to said head fitment portion at said upper portion, such that a portion of the first panel beneath which said interior portion lies is disposed to be in direct contact with the neck of the wearer
   and wherein said pouch portion comprise a length dimension and a width dimension, wherein said width dimension of said pouch portion is defined by an angle α that measures the coextensive extension of said pouch portion about the head of a wearer of such article, wherein α may be any angle between 30 degrees and 300 degrees, including every degree therebetween.

2. An article according to claim 1 wherein at least one of said panel portions includes an opening into which ice may be charged.

3. An article according to claim 2 wherein said opening includes a means for closing said opening that is selected from the group consisting of: hook-and-loop type fasteners, buttons, zippers, and hook-and-eye fasteners.

4. An article as in claim 1 wherein the interior portion that is adapted to contain ice is of such size that the entire volume of the interior portion adapted to contain ice lies beneath more than 50% of the surface area of the panels.

5. An article as in claim 1 wherein the interior portion that is adapted to contain ice is of such size that the entire volume of the interior portion adapted to contain ice lies beneath more than 80% of the surface area of the panels.

6. An article as in claim 1 wherein said pouch portion comprises a plurality of panels which each have a length dimension and a width dimension that define their surface area and the interior portion that is adapted to contain ice is of such size that 80% of the surface area of the panels is used in defining the dimensions of the interior portion.

7. An article as in claim 1 wherein said interior portion of said pouch portion is disposed within said pouch portion such that melted ice exits said pouch portion at its lower portion and contacts the neck of the wearer upon its exit from said pouch.

8. An article as in claim 1 wherein said head fitment portion comprises an article of headwear selected from the group consisting of: visors, baseball caps, cowboy hats, sweatbands, bucket hats, hard hats, and straw hats.

9. An article as in claim 1 wherein said pouch portion comprises a first panel portion that faces the head of its wearer, and a second panel portion that faces away from its wearer, wherein said first panel portion comprises a material that is impervious to water.

10. An article as in claim 1 wherein the first panel portion of said pouch comprises an effective insulative material disposed on its surface which resides within the pouch that is sufficient to preclude a sensation of numbness experienced by the wearer when the pouch portion is charged with ice and said article is worn about the head.

11. An article as in claim 1, further comprising: c) a plastic bag containing ice disposed within the interior portion of said pouch.

12. An article according to claim 1 further comprising: c) ice contained in the interior portion of said pouch.

13. An article as in claim 1 wherein said pouch portion is of a singular construction.

14. An article as in claim 13 wherein said pouch portion is a plastic bag having an upper portion and a lower edge portion, and comprising perforations along its lower edge.

15. An article according to claim 1 wherein the shape of said pouch portion is selected from the group consisting of: rectangular, square, triangular, trapezoidal, rhombohedral, circular, and semicircular.

16. An article according to claim 1 in which the pouch portion has a length dimension of any value between 3.00 inches and 16.00 inches, including every hundredth inch therebetween.

17. An article according to claim 1 wherein the vertex of angle α is located at about the rear of the wearer's head.

18. An article according to claim 1 wherein the interior portion includes a bottom portion and wherein said bottom portion of said interior portion coincides with the lower portion of the pouch.

19. An article according to claim 1 wherein said pouch portion is constructed of a material which permits the passage of water through its walls.

20. An article according to claim 1 wherein said pouch portion is constructed of a material which prevents the passage of water from the interior of said pouch portion to the external surroundings.

21. An article according to claim 1 further comprising: c) ice within said pouch portion.

22. An article according to claim 1 wherein said pouch portion is charged with a material selected from the group consisting of: an ice pack or a coolant-filled pouch.

23. An article according to claim 1 wherein said pouch portion is affixed to said head fitment portion with a closure means selected from the group consisting of: a zipper, a button, a hood-and-loop fastener, or snaps.

24. A headwear article useful for cooling its wearer comprising:
   a) a head fitment portion; and
   b) a pouch portion,
   wherein said pouch portion includes an upper portion, a lower portion, and an interior portion adapted to contain ice, and wherein said pouch portion is affixed to said head fitment portion at the upper portion of said pouch portion, and wherein said pouch portion is disposed sufficiently to be in contact with the neck of said wearer, said panels each having a length dimension and a width dimension that define their surface area and the interior portion that is adapted to contain ice is of such size that at least 75% of the surface area of said panels is used in defining the dimensions of the interior portion
   and wherein said pouch portion comprise a length dimension and a width dimension, wherein said width dimension of said pouch portion is defined by an angle α that measures the coextensive extension of said pouch portion about the head of a wearer of such article, wherein α may be any angle between 30 degrees and 300 degrees, including every degree therebetween.

25. An article according to claim 24 wherein at least 85% of the surface area of the panels is used in defining the dimensions of the interior portion.

26. An article according to claim 24 wherein at least 90% of the surface area of the panels is used in defining the dimensions of the interior portion.

27. A headwear article useful for cooling its wearer comprising:
   a) a head fitment portion; and
   b) a pouch portion,
   wherein said pouch portion includes:
      i) an upper portion;
      ii) a lower portion, and
      iii) an interior portion adapted to contain ice, said interior portion including a bottom portion,
      wherein said bottom portion of said interior portion coincides substantially with the lower portion of the pouch, and wherein said pouch portion is affixed to said head fitment portion at the upper portion of said pouch portion, and wherein said pouch portion is disposed sufficiently to be in contact with the neck of said wearer
      and wherein said pouch portion comprise a length dimension and a width dimension, wherein said width dimension of said pouch portion is defined by an angle $\alpha$ that measures the coextensive extension of said pouch portion about the head of a wearer of such article, wherein $\alpha$ may be any angle between 30 degrees and 300 degrees, including every degree therebetween.

28. A headwear article useful for cooling its wearer comprising:
   a) a head fitment portion; and
   b) a pouch portion,
   wherein said pouch portion includes an upper portion, a lower portion, and an interior portion adapted to contain ice, wherein said pouch portion is a plastic bag of singular construction having an upper portion and a lower edge portion, and having perforations along its lower edge, and wherein said pouch portion is affixed to said head fitment portion at the upper portion of said pouch portion, and wherein said pouch portion is disposed sufficiently to be in contact with the neck of said wearer.

* * * * *